(12) United States Patent
Watson et al.

(10) Patent No.: US 9,888,871 B2
(45) Date of Patent: Feb. 13, 2018

(54) METHODS AND SYSTEMS FOR DETERMINING A VENOUS SIGNAL USING A PHYSIOLOGICAL MONITOR

(71) Applicant: Covidien LP, Mansfield, MA (US)

(72) Inventors: James N. Watson, Dunfermline (GB); Paul S. Addison, Edinburgh (GB)

(73) Assignee: Covidien LP, Mansfield, MA (US)

( * ) Notice: Subject to any disclaimer, the term of this patent is extended or adjusted under 35 U.S.C. 154(b) by 573 days.

(21) Appl. No.: 14/606,919

(22) Filed: Jan. 27, 2015

(65) Prior Publication Data

US 2015/0208965 A1    Jul. 30, 2015

Related U.S. Application Data

(60) Provisional application No. 61/932,666, filed on Jan. 28, 2014.

(51) Int. Cl.
| | | |
|---|---|---|
| *A61B 5/1455* | (2006.01) | |
| *A61B 5/024* | (2006.01) | |
| *A61B 5/1495* | (2006.01) | |
| *A61B 5/021* | (2006.01) | |

(52) U.S. Cl.
CPC ...... *A61B 5/14551* (2013.01); *A61B 5/02416* (2013.01); *A61B 5/02108* (2013.01); *A61B 5/1495* (2013.01)

(58) Field of Classification Search
CPC ............ A61B 5/1455; A61B 5/14551; A61B 5/14552; A61B 5/1495; A61B 5/02108; A61B 5/02416; A61B 5/72; A61B 5/7235; A61B 5/7271
See application file for complete search history.

(56) References Cited

U.S. PATENT DOCUMENTS

| | | | |
|---|---|---|---|
| 5,351,685 | A | 10/1994 | Potratz |
| 5,632,272 | A | 5/1997 | Diab et al. |
| 6,334,065 | B1 | 12/2001 | Al-Ali et al. |
| 6,480,729 | B2 | 11/2002 | Stone |
| 6,985,763 | B2 | 1/2006 | Boas et al. |
| 7,171,251 | B2 | 1/2007 | Sarussi et al. |

(Continued)

OTHER PUBLICATIONS

Allen, J., "Photoplethysmography and its Application in Clinical Physiological Measurement," Physiol. Meas., vol. 28, Mar. 2007, pp. R1-R39.

(Continued)

*Primary Examiner* — Eric Winakur

(57) ABSTRACT

A physiological monitoring system may receive a sensor signal from a physiological sensor. The system may determine a first and second change metric based on the sensor signal, and may determine a venous signal based on the change metrics. In some embodiments, the sensor signal may be a photoplethysmograph signal that includes both arterial and venous information. By subtracting a second change metric from a first change metric, arterial contributions may be substantially removed, resulting in a signal primarily comprising venous information. The venous signal may be indicative of changes in the venous blood, and may be used to determine a physiological parameter, for example, blood pressure. The venous signal may also be used to trigger an event, for example, calibration of a blood pressure measurement.

20 Claims, 6 Drawing Sheets

(56) References Cited

U.S. PATENT DOCUMENTS

| | | | |
|---|---|---|---|
| 7,194,293 B2* | 3/2007 | Baker, Jr. | A61B 5/7221 |
| | | | 600/323 |
| 7,206,621 B2 | 4/2007 | Aoyagi et al. | |
| 7,263,395 B2 | 8/2007 | Chan et al. | |
| 7,706,852 B2* | 4/2010 | Baker, Jr. | A61B 5/14551 |
| | | | 600/323 |
| 7,785,262 B2* | 8/2010 | Melker | A61B 5/14551 |
| | | | 600/484 |
| 8,489,168 B2* | 7/2013 | Kuhn | A61B 5/14551 |
| | | | 600/310 |
| 9,192,330 B2* | 11/2015 | Lin | A61B 5/14552 |
| 9,521,971 B2* | 12/2016 | Lynn | A61B 5/14552 |
| 2004/0087846 A1 | 5/2004 | Wasserman | |
| 2005/0197551 A1 | 9/2005 | Al-Ali et al. | |
| 2006/0224053 A1 | 10/2006 | Black et al. | |
| 2008/0208019 A1 | 8/2008 | Nitzan | |
| 2008/0221463 A1 | 9/2008 | Baker | |
| 2010/0010322 A1 | 1/2010 | Brady | |
| 2011/0004081 A1 | 1/2011 | Addison et al. | |
| 2011/0028854 A1 | 2/2011 | Addison et al. | |
| 2011/0071406 A1 | 3/2011 | Addison et al. | |
| 2012/0150002 A1* | 6/2012 | Shelley | A61B 5/14551 |
| | | | 600/323 |
| 2013/0066175 A1 | 3/2013 | Addison et al. | |
| 2013/0066176 A1* | 3/2013 | Addison | A61B 5/14551 |
| | | | 600/324 |

OTHER PUBLICATIONS

Murray, W. B., and Foster, P. A., "The Peripheral Pulse Wave: Information Overlooked," J. Clin. Monit., vol. 12, Sep. 1996, pp. 365-377.

Shelley, K. H., "Photoplethysmography: Beyond the Calculation of Arterial Oxygen Saturation and Heart Rate," Anesth. Analg., vol. 105, Dec. 2007, pp. S31-S36.

* cited by examiner

US 9,888,871 B2

METHODS AND SYSTEMS FOR DETERMINING A VENOUS SIGNAL USING A PHYSIOLOGICAL MONITOR

CROSS REFERENCE TO RELATED APPLICATION

This application claims the benefit of U.S. Provisional Application No. 61/932,666, filed Jan. 28, 2014, which is hereby incorporated by reference herein in its entirety.

SUMMARY

The present disclosure relates to processing physiological signals, and more particularly relates to determining a venous signal based on a signal received by a pulse oximeter or other physiological monitoring device.

Methods and systems are provided for determining a venous signal based on a received signal. In some embodiments, light signals are received by a system. The system may determine a venous signal based on the received light signals. The venous signal may be calculated by determining one or more change metrics corresponding to the signals. The venous signal may be used to determine a physiological parameter such as, for example, blood pressure. The venous signal may additionally or alternatively be used to trigger an event such as a calibration event, to trigger a physiological measurement (e.g., an auscultatory blood pressure measurement), or as an input to an adaptive filter.

In some embodiments, a method is provided for operating a physiological monitor. The method comprises receiving a physiological signal from a subject, the signal comprising a first component corresponding to a first wavelength of light and a second component corresponding to a second wavelength of light. The method further comprises determining a first change metric based on a change in a baseline of the first component of the physiological signal. The method further comprises determining a second change metric based on a change in a baseline of the second component of the physiological signal and based on a coefficient associated with arterial oxygen saturation. The method further comprises determining a venous signal based on the first change metric and the second change metric, where the venous signal is indicative of changes associated with venous blood. The method further comprises monitoring a physiological parameter based on the venous signal.

In some embodiments, a system is provided for operating a physiological monitor. The system comprises an input configured for receiving a physiological signal from a subject, the signal comprising a first component corresponding to a first wavelength of light and a second component corresponding to a second wavelength of light. The system further comprises one or more processors configured to perform operations. The operations comprise determining a first change metric based on a change in a baseline of the first component of the physiological signal. The operations further comprise determining a second change metric based on a change in a baseline of the second component of the physiological signal and based on a coefficient associated with arterial oxygen saturation. The operations further comprise determining a venous signal based on the first change metric and the second change metric, where the venous signal is indicative of changes associated with venous blood. The operations further comprise monitoring a physiological parameter based on the venous signal.

BRIEF DESCRIPTION OF THE FIGURES

The above and other features of the present disclosure, its nature and various advantages will be more apparent upon consideration of the following detailed description, taken in conjunction with the accompanying drawings in which.

DETAILED DESCRIPTION OF THE FIGURES

Figure 1:
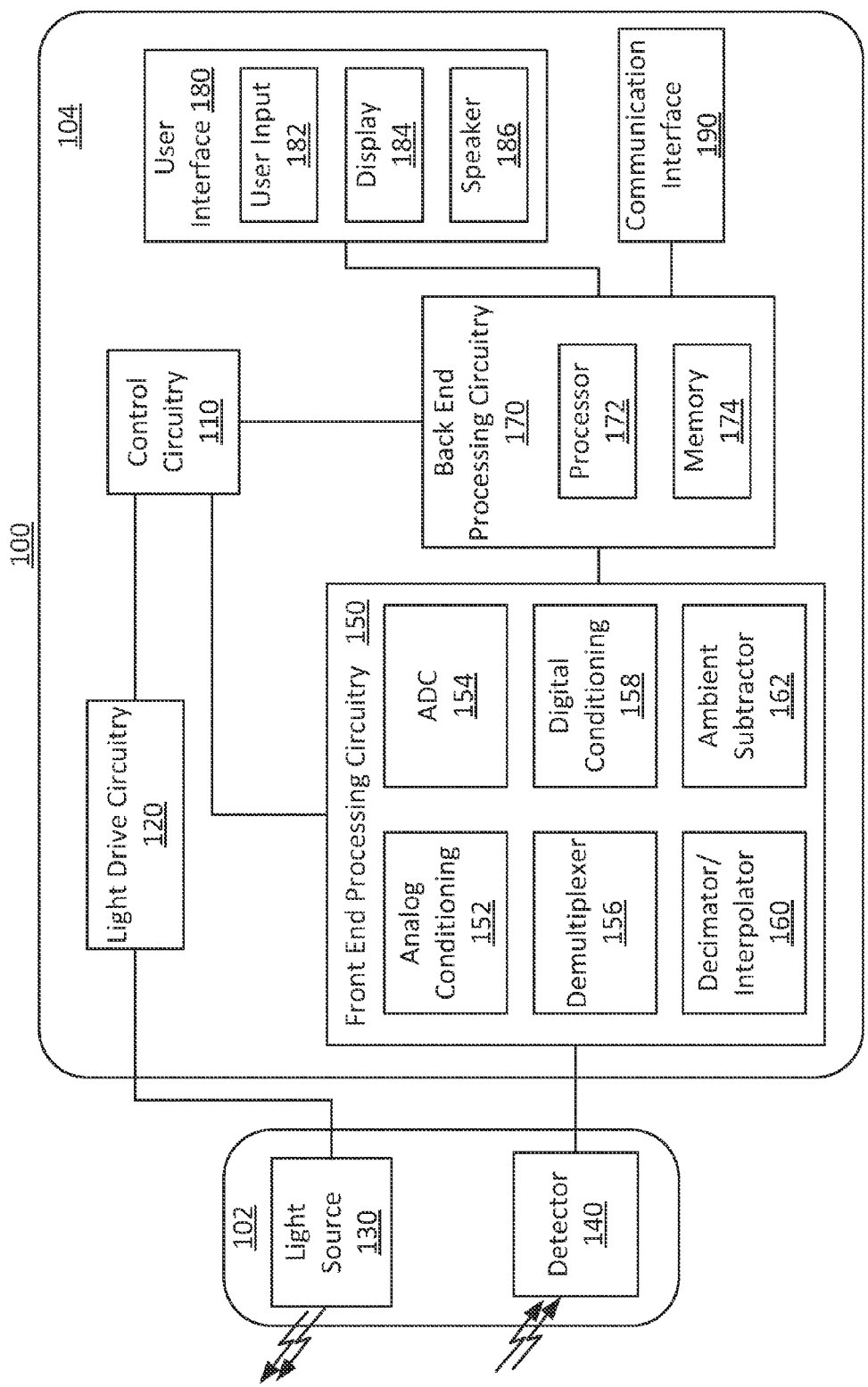
FIG. 1 shows a block diagram of an illustrative physiological monitoring system in accordance with some embodiments of the present disclosure.

The present disclosure is directed towards processing signals in a physiological monitoring system such as a medical device. In particular, a system is configured to determine a venous signal.

A medical device such as a pulse oximeter may receive detected light signals. For example, a light signal may interact with a patient and then be detected using a photodetector. The amplitude and other features of the detected light signal may be used to determine physiological information. For example, physiological changes such as changes in path length or changes in the light absorbance may correspond to changes in the amplitude of the detected signal. These detected light signals are referred to herein as photoplethysmograph (PPG) signals.

In some embodiments, features of a PPG signals are dominated by changes in arterial blood, such as changes in volume and saturation. By determining and compensating for changes in the arterial blood, changes in the venous signal may be analyzed. Changes in the venous signal may correspond to changes in light absorption and/or path length, and thus may correspond to changes in the oxygen saturation of venous blood and/or the amount of venous blood at the sample site. In some embodiments, venous signals may provide information such as blood pressure information, cardiac output (CO), central venous pressure (CVP), systemic vascular resistance (SVR), mean arterial pressure (MAP), oxygen demand, any other suitable parameter, or any combination thereof. For example, venous signals may provide information that can contribute to the determination of such parameters. In some embodiments, these parameters may be determined based on a venous signal and one or more additional sensors such as an arterial pressure catheter or blood pressure cuff. In some embodiments, the venous signal may be used to provide information and/or confidence metrics for relationships between the aforementioned parameters where not all of the information is known.

As used herein, cardiac output generally refers to the volume of blood pumped by the heart. As used herein, systemic vascular resistance generally refers to the resistance generated by peripheral circulation. As used herein central venous pressure generally refers to the pressure of blood in the thoracic vena cava, and reflects the amount of blood returning to the heart. As used herein, mean arterial pressure generally refers to the average blood pressure during a cardiac cycle. As used herein, vasocompliance generally refers to the compliance of blood vessels.

In some embodiments, a detected signal, such as a PPG signal, may have an AC component and a DC component. As used herein, the AC component corresponds to the portion of the signal that varies over time. As used herein, the DC component corresponds to the portion of the signal that remains relatively constant over time. For example, a 1V AC sine wave with a 5V offset may vary between 4V and 6V. In some embodiments, this may be considered a 4V DC component, because that portion of the signal is relatively unchanging, and a 2V AC component, because that portion of the signal is changing.

The following mathematical expressions (1)-(20) provide an exemplary derivation of a venous signal.

In some embodiments, an $SpO_2$ value may be determined by determining a ratios-of-ratios value. The following mathematical expressions (1)-(6) provide an exemplary derivation of the ratio-of-ratios equation. The amount of IR light received by a detector may be expressed, using the Beer-Lambert Law, as:

$$I_{IR,max} = I_{IR,0} \cdot e^{-(\lambda_{HHb,IR} c_{HHb}^{Art} + \lambda_{OHb,IR} c_{OHb}^{Art}) d_{Art}} \cdot e^{-(\lambda_{HHb,IR} c_{HHb}^{Ven} + \lambda_{OHb,IR} c_{OHb}^{Ven}) d_{Ven}} \cdot e^{-(\lambda_{static,IR} c_{static}) d_{static}} \quad (1)$$

where $I_{IR,max}$ is the maximum received light intensity, $I_{IR,0}$ is the intensity of the transmitted light, Art refers to arterial blood, Ven refers to venous blood, and the exponential terms correspond to the absorbance of light by oxyhemoglobin (OHb), deoxyhemoglobin (HHb), and static light absorbers. In equation (1), $\lambda$ corresponds to the absorption coefficient for a given wavelength and light absorber, c corresponds to the concentration of a particular absorber, $d_{Art}$ corresponds to the arterial path length, $d_{Ven}$ corresponds to the venous path length, and $d_{Static}$ corresponds to the static path length. The maximum received light intensity occurs when there is the least amount of absorption. With regards to pulsing blood, $I_{max}$ occurs at the diastole, when there is the smallest amount of blood interacting with the light. Accordingly, as used herein, the DC component of the signal refers to the amount of light received at diastole. As used herein, the AC component of the signal refers to the intensity not included in the DC component. Thus in some embodiments, $I = I_{AC} + I_{DC}$.

The minimum received light intensity, $I_{IR,min}$, may be expressed as:

$$I_{IR,min} = I_{IR,0} \cdot e^{-(\lambda_{HHb,IR} c_{HHb}^{Art} + \lambda_{OHb,IR} c_{OHb}^{Art}) \Delta d_{Art}} \cdot e^{-(\lambda_{HHb,IR} c_{HHb}^{Art} + \lambda_{OHb,IR} c_{OHb}^{Art}) d_{Art}} \cdot e^{-(\lambda_{HHb,IR} c_{HHb}^{Ven} + \lambda_{OHb,IR} c_{OHb}^{Ven}) d_{Ven}} \cdot e^{-(\lambda_{static,IR} c_{static}) d_{static}} \quad (2)$$

that is, the expression $I_{IR,max}$, less the first exponential term, which corresponds to the change in the arterial path length. Combining equations (1) and (2) provides:

$$\frac{I_{IR,min}}{I_{IR,max}} = e^{-(\lambda_{HHb,IR} c_{HHb,Art} + \lambda_{OHb,IR} c_{OHb,Art}) \Delta d_{Art}} \quad (3)$$

Repeating the calculations for a red light signal provides:

$$\frac{I_{R,min}}{I_{R,max}} = e^{-(\lambda_{HHb,R} c_{HHb}^{Art} + \lambda_{OHb,R} c_{OHb}^{Art}) \Delta d_{Art}} \quad (4)$$

The ratio-of-ratios term R may be determined by combining equations (3) and (4):

$$\frac{\ln\left|\frac{I_{R,min}}{I_{R,max}}\right|}{\ln\left|\frac{I_{IR,min}}{I_{IR,max}}\right|} = \frac{(\lambda_{HHb,R} c_{HHb}^{Art} + \lambda_{OHb,R} c_{OHb}^{Art})}{(\lambda_{HHb,IR} c_{HHb}^{Art} + \lambda_{OHb,IR} c_{OHb}^{Art})} = R \quad (5)$$

which may be approximated for small changes in received light intensity (e.g., when $I_{x,AC}/I_{x,max}$ is small, for example, much less than 1) as the first term of the Maclaurin series:

$$R = \frac{\ln\left|\frac{I_{R,min}}{I_{R,max}}\right|}{\ln\left|\frac{I_{IR,min}}{I_{IR,max}}\right|} = \frac{\ln\left|1 + \frac{I_{R,AC}}{I_{R,max}}\right|}{\ln\left|1 + \frac{I_{IR,AC}}{I_{IR,max}}\right|} \approx \frac{\left(\frac{I_{R,AC}}{I_{R,DC}}\right)}{\left(\frac{I_{IR,AC}}{I_{IR,DC}}\right)} \quad (6)$$

In some embodiments, the ratio-of-ratios term R may correspond to arterial blood oxygen saturation. While R is described above as being derived from maximum and minimum received light intensities, it will be understood that any differences in received light intensities may be used assuming the differences are caused by changes in the effective path length in the artery. In other words, the changes are assumed to be caused by changes in arterial volume (e.g., due to an arterial pulse). In some embodiments, for example when the system is implemented in a pulse oximeter, R may be obtained from an oximetry algorithm.

In some embodiments, the DC component of the signal may be expressed as:

$$I_{IR,DC} = I_{IR,0} \cdot e^{-(\lambda_{HHb,IR} c_{HHb}^{Art} + \lambda_{OHb,IR} c_{OHb}^{Art}) d_{Art}} \cdot e^{-(\lambda_{HHb,IR} c_{HHb}^{Ven} + \lambda_{OHb,IR} c_{OHb}^{Ven}) d_{Ven}} \cdot e^{-(\lambda_{static,IR} c_{static}) d_{static}} \quad (7)$$

The DC component may be equal to equation (1), that is, $I_{IR,max}$ or may be equal to the received light intensity at any point in the pulse cycle. The ratio of $I_{IR,DC}$ at time $t_1$ to time $t_2$ may be expressed as:

$$\frac{I(t_1)_{IR,DC}}{I(t_2)_{IR,DC}} = \frac{I_{IR,0} \cdot e^{-(\lambda_{HHb,IR} c_{HHb}^{Art} + \lambda_{OHb,IR} c_{OHb}^{Art}) d_{Art1}} \cdot e^{-(\lambda_{HHb,IR} c_{HHb}^{Ven,t1} + \lambda_{OHb,IR} c_{OHb}^{Ven,t1}) d_{Ven1}} \cdot e^{-(\lambda_{static,IR} c_{static}) d_{static}}}{I_{IR,0} \cdot e^{-(\lambda_{HHb,IR} c_{HHb}^{Art} + \lambda_{OHb,IR} c_{OHb}^{Art}) d_{Art2}} \cdot e^{-(\lambda_{HHb,IR} c_{HHb}^{Ven,t2} + \lambda_{OHb,IR} c_{OHb}^{Ven,t2}) d_{Ven2}} \cdot e^{-(\lambda_{static,IR} c_{static}) d_{static}}} \quad (8)$$

and assuming that static absorption terms remain constant, may be simplified to:

$$\frac{I(t_1)_{IR,DC}}{I(t_2)_{IR,DC}} = \frac{e^{-(\lambda_{HHb,IR} c_{HHb}^{Art} + \lambda_{OHb,IR} c_{OHb}^{Art}) d_{Art1}} \cdot e^{-(\lambda_{HHb,IR} c_{HHb}^{Ven,t1} + \lambda_{OHb,IR} c_{OHb}^{Ven,t1}) d_{Ven1}}}{e^{-(\lambda_{HHb,IR} c_{HHb}^{Art} + \lambda_{OHb,IR} c_{OHb}^{Art}) d_{Art2}} \cdot e^{-(\lambda_{HHb,IR} c_{HHb}^{Ven,t2} + \lambda_{OHb,IR} c_{OHb}^{Ven,t2}) d_{Ven2}}} \quad (9)$$

which may be approximated, assuming the arterial concentration remains relatively constant, as:

$$\ln\left(\frac{I(t_1)_{IR,DC}}{I(t_2)_{IR,DC}}\right) + (\lambda_{HHb,IR}c_{HHb}^{Ven,t1} + \lambda_{OHb,IR}c_{OHb}^{Ven,t1})d_{Ven1} - \quad (10)$$

$$(\lambda_{HHb,IR}c_{HHb}^{Ven,t2} + \lambda_{OHb,IR}c_{OHb}^{Ven,t2})d_{Ven2} =$$

$$(\lambda_{HHb,IR}c_{HHb}^{Art} + \lambda_{OHb,IR}c_{OHb}^{Art})\Delta d_{Art}$$

The ratio of equation (10) with the corresponding red light calculation may be expressed as:

$$\frac{\left(\frac{\Delta I_{R,DC}}{I_{R,DC}}\right) + (\lambda_{HHb,R}c_{HHb}^{Ven,t1} + \lambda_{OHb,R}c_{OHb}^{Ven,t1})d_{Ven1} - (\lambda_{HHb,R}c_{HHb}^{Ven,t2} + \lambda_{OHb,R}c_{OHb}^{Ven,t2})d_{Ven2}}{\left(\frac{\Delta I_{R,DC}}{I_{R,DC}}\right) + (\lambda_{HHc,IR}c_{HHb}^{Ven,t1} + \lambda_{OHb,IR}c_{OHb}^{Ven,t1})d_{Ven1} - (\lambda_{HHb,IR}c_{HHb}^{Ven,t2} + \lambda_{OHb,IR}c_{OHb}^{Ven,t2})d_{Ven2}} \quad (11)$$

$$R = \frac{(\lambda_{HHb,R}c_{HHb}^{Art} + \lambda_{OHb,R}c_{OHb}^{Art})\Delta d_{Art}}{(\lambda_{HHb,IR}c_{HHb}^{Art} + \lambda_{OHb,IR}c_{OHb}^{Art})\Delta d_{Art}}$$

where R is the ratio-of-ratios term described by equations (5) and (6).

Equation (11) may be rearranged to provide equation (12):

$$\left(\frac{\Delta I_{R,DC}}{I_{R,DC}}\right) - R\left(\frac{\Delta I_{IR,DC}}{I_{IR,DC}}\right) = \quad (12)$$

$$(c_{HHb}^{Ven,t1}d_{Ven1} - c_{HHb}^{Ven,t2}d_{Ven2})(R\lambda_{HHb,IR} - \lambda_{HHb,R}) +$$

$$(c_{OHb}^{Ven,t1}d_{Ven1} - c_{OHb}^{Ven,t2}d_{Ven2})(R\lambda_{OHb,IR} - \lambda_{OHb,R})$$

Equation (5) may be factored and rearranged to provide equation (13):

$$c_{HHb}(\lambda_{HHb,R} - R\lambda_{HHb,IR}) = c_{OHb}(R\lambda_{OHb,IR} - \lambda_{OHb,R}) \quad (13)$$

Equations (12) and (13) may be combined to provide equation (14):

$$\frac{\left(\frac{\Delta I_{R,DC}}{I_{R,DC}}\right) - R\left(\frac{\Delta I_{IR,DC}}{I_{IR,DC}}\right)}{(\lambda_{HHb,R} - R\lambda_{HHb,IR})} = \quad (14)$$

$$(c_{HHb}^{Ven,t2}d_{Ven2} - c_{HHb}^{Ven,t1}d_{Ven1}) + \frac{c_{HHb}^{Art}}{c_{OHb}^{Art}}(c_{OHb}^{Ven,t1}d_{Ven1} - c_{OHb}^{Ven,t2}d_{Ven2})$$

Expressing arterial saturation s as a ratio of the oxyhemoglobin concentration to the total hemoglobin concentration results in:

$$s = \frac{c_{OHb}}{c_{HHb} + c_{OHb}} \quad (15)$$

$$1 - s = \frac{c_{HHb}}{c_{HHb} + c_{OHb}} \quad (16)$$

which can be combined to provide:

$$\frac{c_{HHb}^{Art}}{c_{OHb}^{Art}} = \frac{\left(\frac{c_{HHb}}{c_{HHb} + c_{OHb}}\right)}{\left(\frac{c_{OHb}}{c_{HHb} + c_{OHb}}\right)} = \left(\frac{1-s}{s}\right) = \left(\frac{1}{s} - 1\right) \quad (17)$$

Combining equations (14) and (17) provides:

$$\frac{\left(\frac{\Delta I_{R,DC}}{I_{R,DC}}\right) - R\left(\frac{\Delta I_{IR,DC}}{I_{IR,DC}}\right)}{(\lambda_{HHb,R} - R\lambda_{HHb,IR})} = \quad (18)$$

$$(c_{HHb}^{Ven,t2}d_{Ven2} - c_{HHb}^{Ven,t1}d_{Ven1}) + \left(\frac{1}{s} - 1\right)(c_{OHb}^{Ven,t1}d_{Ven1} - c_{OHb}^{Ven,t2}d_{Ven2})$$

When saturation is relatively high (i.e., s is close to 1), the rightmost expression of (18) may be considered to be approximately zero and equation (18) may be approximated as:

$$\frac{\left(\frac{\Delta I_{R,DC}}{I_{R,DC}}\right) - R\left(\frac{\Delta I_{IR,DC}}{I_{IR,DC}}\right)}{(\lambda_{HHb,R} - R\lambda_{HHb,IR})} = (c_{HHb}^{Ven,t2}d_{V2} - c_{HHb}^{Ven,t1}d_{V1}) \quad (19)$$

In some embodiments, equation (19) may be considered a venous signal. The right hand side of equation (19) includes the difference in the concentration of venous deoxyhemoglobin between times $t_1$ and $t_2$, based on the change in path length $d_{ven}$. The denominator of the left hand side is constant when R is constant, and thus the numerator of the equation may be proportional to changes in the venous deoxyhemoglobin concentration and/or changes in the venous path length, which effectively corresponds to changes in venous volume at the sample site.

In some embodiments, subtracting the second term from the first term in the numerator of equation (19) removes the arterial contribution and provides primarily venous information. In an example, when there is little or no change in the arterial concentration and saturation is high (i.e., there is little or no arterial deoxyhemoglobin (HHb)), then any change in the venous signal that is associated with changes in HHb must primarily correspond to changes in HHb concentration or volume on the venous side. Thus in some embodiments, the expression:

$$\frac{\left(\frac{\Delta I_{R,DC}}{I_{R,DC}}\right) - R\left(\frac{\Delta I_{IR,DC}}{I_{IR,DC}}\right)}{(\lambda_{HHb,R} - R\lambda_{HHb,IR})} \quad (20)$$

may be used to track changes in the venous blood (e.g., venous saturation and/or venous volume).

The foregoing techniques may be implemented in an oximeter. An oximeter is a medical device that may determine the oxygen saturation of an analyzed tissue. One common type of oximeter is a pulse oximeter, which may non-invasively measure the oxygen saturation of a patient's blood (as opposed to measuring oxygen saturation invasively by analyzing a blood sample taken from the patient). Pulse oximeters may be included in patient monitoring systems that measure and display various blood flow characteristics including, but not limited to, the blood oxygen saturation (e.g., arterial, venous, or both). Such patient monitoring systems, in accordance with the present disclosure, may also measure and display additional or alternative physiological parameters such as pulse rate, respiration rate, respiration effort, blood pressure, hemoglobin concentration (e.g., oxygenated, deoxygenated, and/or total), systemic vascular resistance, mean arterial pressure, cardiac output, central venous pressure, oxygen demand, adaptive filter parameters, any other suitable physiological parameters, or any combination thereof. Exemplary embodiments of determining respiration rate are disclosed in Addison et al. U.S. Patent Publication No. 2011/0071406, published Mar. 24, 2011, which is hereby incorporated by reference herein in its entirety. Exemplary embodiments of determining respiration effort are disclosed in Addison et al. U.S. Patent Publication No. 2011/0004081, published Jan. 6, 2011, which is hereby incorporated by reference herein in its entirety. Exemplary embodiments of determining blood pressure are disclosed in Addison et al. U.S. Patent Publication No. 2011/0028854, published Feb. 3, 2011, which is hereby incorporated by reference herein in its entirety.

Pulse oximetry may be implemented using a photoplethysmograph. Pulse oximeters and other photoplethysmograph devices may also be used to determine other physiological parameter and information as disclosed in: J. Allen, "Photoplethysmography and its application in clinical physiological measurement," *Physiol. Meas.*, vol. 28, pp. R1-R39, March 2007; W. B. Murray and P. A. Foster, "The peripheral pulse wave: information overlooked," *J. Clin. Monit.*, vol. 12, pp. 365-377, September 1996; and K. H. Shelley, "Photoplethysmography: beyond the calculation of arterial oxygen saturation and heart rate," *Anesth. Analg.*, vol. 105, pp. S31-S36, December 2007; all of which are incorporated by reference herein in their entireties.

An oximeter may include a light sensor that is placed at a site on a patient, typically a fingertip, toe, forehead or earlobe, or in the case of a neonate, across a foot or hand. The oximeter may use a light source to pass light through blood perfused tissue and photoelectrically sense the absorption of the light in the tissue. Additional suitable sensor locations include, without limitation, the neck to monitor carotid artery pulsatile flow, the wrist to monitor radial artery pulsatile flow, the inside of a patient's thigh to monitor femoral artery pulsatile flow, the ankle to monitor tibial artery pulsatile flow, around or in front of the ear, and locations with strong pulsatile arterial flow. Suitable sensors for these locations may include sensors that detect reflected light.

The oximeter may measure the intensity of light that is received at the light sensor as a function of time. The oximeter may also include sensors at multiple locations. A signal representing light intensity versus time or a mathematical manipulation of this signal (e.g., a scaled version thereof, a log taken thereof, a scaled version of a log taken thereof, an inverted signal, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate any of a number of physiological parameters, including an amount of a blood constituent (e.g., oxyhemoglobin) being measured as well as a pulse rate and when each individual pulse occurs.

In some embodiments, the photonic signal interacting with the tissue is of one or more wavelengths that are attenuated by the blood in an amount representative of the blood constituent concentration. Red and infrared (IR) wavelengths may be used because it has been observed that highly oxygenated blood will absorb relatively less red light and more IR light than blood with a lower oxygen saturation. By comparing the intensities of two wavelengths at different points in the pulse cycle, it is possible to estimate the blood oxygen saturation of hemoglobin in arterial blood.

The system may process data to determine physiological parameters using techniques well known in the art. For example, the system may determine blood oxygen saturation using two wavelengths of light and a ratio-of-ratios calculation. The system also may identify pulses and determine pulse amplitude, respiration, blood pressure, other suitable parameters, or any combination thereof, using any suitable calculation techniques. In some embodiments, the system may use information from external sources (e.g., tabulated data, secondary sensor devices) to determine physiological parameters.

In some embodiments, a light drive modulation may be used. For example, a first light source may be turned on for a first drive pulse, followed by an off period, followed by a second light source for a second drive pulse, followed by an off period. The first and second drive pulses may be used to determine physiological parameters. The off periods may be used to detect ambient signal levels, reduce overlap of the light drive pulses, allow time for light sources to stabilize, allow time for detected light signals to stabilize or settle, reduce heating effects, reduce power consumption, for any other suitable reason, or any combination thereof.

It will be understood that the techniques described herein are not limited to pulse oximeters and may be applied to any suitable physiological monitoring device.

The following description and accompanying FIGS. 1-6 provide additional details and features of some embodiments of the present disclosure.

FIG. 1 shows a block diagram of illustrative physiological monitoring system 100 in accordance with some embodiments of the present disclosure. System 100 may include a sensor 102 and a monitor 104 for generating and processing sensor signals that include physiological information of a subject. In some embodiments, sensor 102 and monitor 104 may be part of an oximeter.

Sensor 102 of physiological monitoring system 100 may include light source 130 and detector 140. Light source 130 may be configured to emit photonic signals having one or more wavelengths of light (e.g. red and IR) into a subject's tissue. For example, light source 130 may include a red light emitting light source and an IR light emitting light source, e.g. red and IR light emitting diodes (LEDs), for emitting light into the tissue of a subject to generate sensor signals that include physiological information. In one embodiment, the red wavelength may be between about 600 nm and about 750 nm, and the IR wavelength may be between about 800 nm and about 1000 nm. It will be understood that light source 130 may include any number of light sources with any suitable characteristics. In embodiments where an array of sensors is used in place of single sensor 102, each sensor may be configured to emit a single wavelength. For example, a first sensor may emit only a red light while a second may emit only an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 140 may be chosen to be specifically sensitive to the chosen targeted energy spectrum of light source 130.

In some embodiments, detector 140 may be configured to detect the intensity of light at the red and IR wavelengths. In some embodiments, an array of sensors may be used and each sensor in the array may be configured to detect an intensity of a single wavelength. In operation, light may enter detector 140 after passing through the subject's tissue. Detector 140 may convert the intensity of the received light into an electrical signal. The light intensity may be directly related to the absorbance and/or reflectance of light in the tissue. That is, when more light at a certain wavelength is absorbed or reflected, less light of that wavelength is received from the tissue by detector 140. After converting the received light to an electrical signal, detector 140 may send the detection signal to monitor 104, where the detection signal may be processed and physiological parameters may be determined (e.g., based on the absorption of the red and IR wavelengths in the subject's tissue). In some embodiments, the detection signal may be preprocessed by sensor 102 before being transmitted to monitor 104.

In the embodiment shown, monitor 104 includes control circuitry 110, light drive circuitry 120, front end processing circuitry 150, back end processing circuitry 170, user interface 180, and communication interface 190. Monitor 104 may be communicatively coupled to sensor 102 using, for example, one or more inputs.

Control circuitry 110 may be coupled to light drive circuitry 120, front end processing circuitry 150, and back end processing circuitry 170, and may be configured to control the operation of these components. In some embodiments, control circuitry 110 may be configured to provide timing control signals to coordinate their operation. For example, light drive circuitry 120 may generate a light drive signal, which may be used to turn on and off the light source 130, based on the timing control signals. The front end processing circuitry 150 may use the timing control signals to operate synchronously with light drive circuitry 120. For example, front end processing circuitry 150 may synchronize the operation of an analog-to-digital converter and a demultiplexer with the light drive signal based on the timing control signals. In addition, the back end processing circuitry 170 may use the timing control signals to coordinate its operation with front end processing circuitry 150.

Light drive circuitry 120, as discussed above, may be configured to generate a light drive signal that is provided to light source 130 of sensor 102. The light drive signal may, for example, control the intensity of light source 130 and the timing of when light source 130 is turned on and off. In some embodiments, light drive circuitry 120 may comprise a power supply and a switch for selectively applying power to light source 130. When light source 130 is configured to emit two or more wavelengths of light, the light drive signal may be configured to control the operation of each wavelength of light. The light drive signal may comprise a single signal or may comprise multiple signals (e.g., one signal for each wavelength of light). An illustrative light drive signal is shown in FIG. 2A.

In some embodiments, control circuitry 110 and light drive circuitry 120 may generate light drive parameters based on a metric. For example, back end processing 170 may receive information about received light signals, determine light drive parameters based on that information, and send corresponding information to control circuitry 110.

Figure 2A:
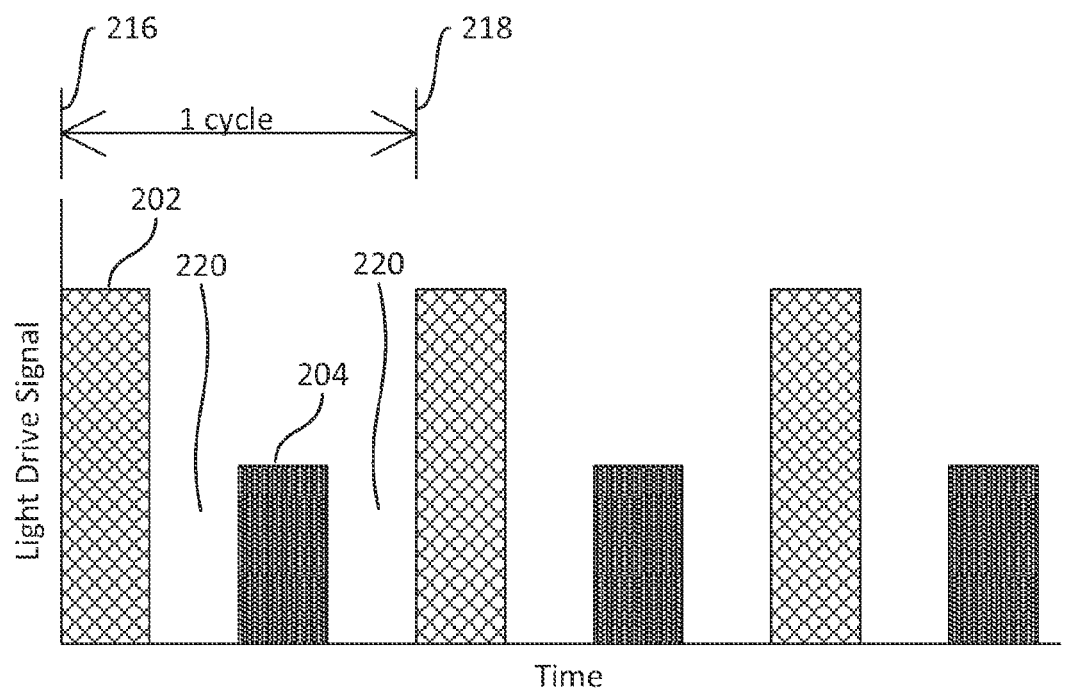
FIG. 2A shows an illustrative plot of a light drive signal in accordance with some embodiments of the present disclosure.

FIG. 2A shows an illustrative plot of a light drive signal including red light drive pulse 202 and IR light drive pulse 204 in accordance with some embodiments of the present disclosure. Light drive pulses 202 and 204 are illustrated as square waves. These pulses may include shaped waveforms rather than a square wave. The shape of the pulses may be generated by a digital signal generator, digital filters, analog filters, any other suitable equipment, or any combination thereof. For example, light drive pulses 202 and 204 may be generated by light drive circuitry 120 under the control of control circuitry 110. As used herein, drive pulses may refer to the high and low states of a shaped pulse, switching power or other components on and off, high and low output states, high and low values within a continuous modulation, other suitable relatively distinct states, or any combination thereof. The light drive signal may be provided to light source 130, including red light drive pulse 202 and IR light drive pulse 204 to drive red and IR light emitters, respectively, within light source 130. Red light drive pulse 202 may have a higher amplitude than IR light drive pulse 204 since red LEDs may be less efficient than IR LEDs at converting electrical energy into light energy. In some embodiments, the output levels may be equal, may be adjusted for nonlinearity of emitters, may be modulated in any other suitable technique, or any combination thereof. Additionally, red light may be absorbed and scattered more than IR light when passing through perfused tissue.

When the red and IR light sources are driven in this manner they emit pulses of light at their respective wavelengths into the tissue of a subject in order generate sensor signals that include physiological information that physiological monitoring system 100 may process to calculate physiological parameters. It will be understood that the light drive amplitudes of FIG. 2A are merely exemplary and that any suitable amplitudes or combination of amplitudes may be used, and may be based on the light sources, the subject tissue, the determined physiological parameter, modulation techniques, power sources, any other suitable criteria, or any combination thereof.

The light drive signal of FIG. 2A may also include "off" periods 220 between the red and IR light drive pulse. "Off" periods 220 are periods during which no drive current may be applied to light source 130. "Off" periods 220 may be provided, for example, to prevent overlap of the emitted light, since light source 130 may require time to turn completely on and completely off. The period from time 216 to time 218 may be referred to as a drive cycle, which includes four segments: a red light drive pulse 202, followed by an "off" period 220, followed by an IR light drive pulse 204, and followed by an "off" period 220. After time 218, the drive cycle may be repeated (e.g., as long as a light drive signal is provided to light source 130). It will be understood that the starting point of the drive cycle is merely illustrative and that the drive cycle can start at any location within FIG. 2A, provided the cycle spans two drive pulses and two "off" periods. Thus, each red light drive pulse 202 and each IR light drive pulse 204 may be understood to be surrounded by two "off" periods 220. "Off" periods may also be referred to as dark periods, in that the emitters are dark or returning to dark during that period. It will be understood that the particular square pulses illustrated in FIG. 2A are merely exemplary and that any suitable light drive scheme is possible. For example, light drive schemes may include shaped pulses, sinusoidal modulations, time division multiplexing other than as shown, frequency division multiplexing, phase division multiplexing, any other suitable light drive scheme, or any combination thereof.

Referring back to FIG. 1, front end processing circuitry 150 may receive a detection signal from detector 140 and provide one or more processed signals to back end processing circuitry 170. In some embodiments, front end processing circuitry 150 may receive the detection signals from one or more inputs of monitor 104. The term "detection signal," as used herein, may refer to any of the signals generated within front end processing circuitry 150 as it processes the output signal of detector 140. Front end processing circuitry 150 may perform various analog and digital processing of the detector signal. One suitable detector signal that may be received by front end processing circuitry 150 is shown in FIG. 2B.

Figure 2B:
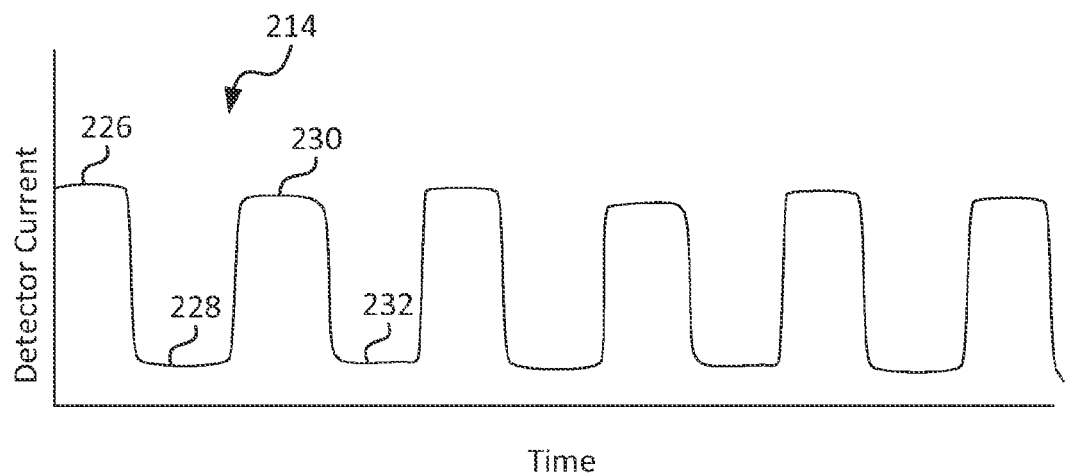
FIG. 2B shows an illustrative plot of a detector signal that may be generated by a sensor in accordance with some embodiments of the present disclosure.

FIG. 2B shows an illustrative plot of detector current waveform 214 that may be generated by a sensor in accordance with some embodiments of the present disclosure. The peaks of detector current waveform 214 may represent current signals provided by a detector, such as detector 140 of FIG. 1, when light is being emitted from a light source. The amplitude of detector current waveform 214 may be proportional to the light incident upon the detector. The peaks of detector current waveform 214 may be synchronous with drive pulses driving one or more emitters of a light source, such as light source 130 of FIG. 1. For example, detector current peak 226 may be generated in response to a light source being driven by red light drive pulse 202 of FIG. 2A, and peak 230 may be generated in response to a light source being driven by IR light drive pulse 204. Valley 228 of detector current waveform 214 may be synchronous with periods of time during which no light is being emitted by the light source, or the light source is returning to dark, such as "off" period 220. While no light is being emitted by a light source during the valleys, detector current waveform 214 may not fall all of the way to zero.

It will be understood that detector current waveform 214 may be an at least partially idealized representation of a detector signal, assuming perfect light signal generation, transmission, and detection. It will be understood that an actual detector current will include amplitude fluctuations, frequency deviations, droop, overshoot, undershoot, rise time deviations, fall time deviations, other deviations from the ideal, or any combination thereof. It will be understood that the system may shape the drive pulses shown in FIG. 2A in order to make the detector current as similar as possible to idealized detector current waveform 214.

Referring back to FIG. 1, front end processing circuitry 150, which may receive a detection signal, such as detector current waveform 214, may include analog conditioning 152, analog-to-digital converter (ADC) 154, demultiplexer 156, digital conditioning 158, decimator/interpolator 160, and ambient subtractor 162.

Analog conditioning 152 may perform any suitable analog conditioning of the detector signal. The conditioning performed may include any type of filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof.

The conditioned analog signal may be processed by analog-to-digital converter 154, which may convert the conditioned analog signal into a digital signal. Analog-to-digital converter 154 may operate under the control of control circuitry 110. Analog-to-digital converter 154 may use timing control signals from control circuitry 110 to determine when to sample the analog signal. Analog-to-digital converter 154 may be any suitable type of analog-to-digital converter of sufficient resolution to enable a physiological monitor to accurately determine physiological parameters.

Demultiplexer 156 may operate on the analog or digital form of the detector signal to separate out different components of the signal. For example, detector current waveform 214 of FIG. 2B includes a red component corresponding to peak 226, an IR component corresponding to peak 230, and at least one ambient component corresponding to valley 232. Demultiplexer 156 may operate on detector current waveform 214 of FIG. 2B to generate a red signal, an IR signal, a first ambient signal (e.g., corresponding to the ambient component corresponding to valley 228 that occurs immediately after the peak 226), and a second ambient signal (e.g., corresponding to the ambient component corresponding to valley 232 that occurs immediately after the IR component 230). Demultiplexer 156 may operate under the control of control circuitry 110. For example, demultiplexer 156 may use timing control signals from control circuitry 110 to identify and separate out the different components of the detector signal.

Digital conditioning 158 may perform any suitable digital conditioning of the detector signal. Digital conditioning 158 may include any type of digital filtering of the signal (e.g., low pass, high pass, band pass, notch, or any other suitable filtering), amplifying, performing an operation on the signal, performing any other suitable digital conditioning, or any combination thereof.

Decimator/interpolator 160 may decrease the number of samples in the digital detector signal. For example, decimator/interpolator 160 may decrease the number of samples by removing samples from the detector signal or replacing samples with a smaller number of samples. The decimation or interpolation operation may include or be followed by filtering to smooth the output signal.

Ambient subtractor 162 may operate on the digital signal. In some embodiments, ambient subtractor 162 may remove dark or ambient contributions to the received signal.

The components of front end processing circuitry 150 are merely illustrative and any suitable components and combinations of components may be used to perform the front end processing operations.

The front end processing circuitry 150 may be configured to take advantage of the full dynamic range of analog-to-digital converter 154. This may be achieved by applying gain to the detection signal, by analog conditioning 152 to map the expected range of the signal to the full or close to full output range of analog-to-digital converter 154. The output value of analog-to-digital converter 154, as a function of the total analog gain applied to the detection signal, may be given as:

$$\text{ADC Value} = \text{Total Analog Gain} \times [\text{Ambient Light} + \text{LED Light}] \quad (21)$$

Ideally, when ambient light is zero and when the light source is off, the analog-to-digital converter 154 will read just above the minimum input value. When the light source is on, the total analog gain may be set such that the output of analog-to-digital converter 154 may read close to the full scale of analog-to-digital converter 154 without saturating. This may allow the full dynamic range of analog-to-digital converter 154 to be used for representing the detection signal, thereby increasing the resolution of the converted signal. In some embodiments, the total analog gain may be reduced by a small amount so that small changes in the light level incident on the detector do not cause saturation of analog-to-digital converter 154.

However, if the contribution of ambient light is large relative to the contribution of light from a light source, the total analog gain applied to the detection current may need to be reduced to avoid saturating analog-to-digital converter 154. When the analog gain is reduced, the portion of the signal corresponding to the light source may map to a smaller number of analog-to-digital conversion bits. Thus, more ambient light noise in the input of analog-to-digital converter 154 may results in fewer bits of resolution for the portion of the signal from the light source. This may have a detrimental effect on the signal-to-noise ratio of the detection signal. Accordingly, passive or active filtering or signal modification techniques may be employed to reduce the effect of ambient light on the detection signal that is applied to analog-to-digital converter 154, and thereby reduce the contribution of the noise component to the converted digital signal.

Back end processing circuitry 170 may include processor 172 and memory 174. Processor 172 may be adapted to execute software, which may include an operating system and one or more applications, as part of performing the functions described herein. Processor 172 may receive and further process sensor signals received from front end processing circuitry 150. For example, processor 172 may determine one or more physiological parameters based on the received physiological signals. Processor 172 may include an assembly of analog or digital electronic components. Processor 172 may calculate physiological information. For example, processor 172 may compute one or more of a venous signal, a blood oxygen saturation (e.g., arterial, venous, or both), pulse rate, respiration rate, respiration effort, blood pressure, hemoglobin concentration (e.g., oxygenated, deoxygenated, and/or total), any other suitable physiological parameters, or any combination thereof. In some embodiments, a venous signal may be used to estimate changes in systemic vascular resistance, mean arterial pressure, cardiac output, central venous pressure, oxygen demand, may be used as an input to an adaptive filter, may be used for any other suitable purpose, or any combination thereof. Processor 172 may perform any suitable signal processing of a signal, such as any suitable band-pass filtering, adaptive filtering, closed-loop filtering, any other suitable filtering, and/or any combination thereof. Processor 172 may also receive input signals from additional sources not shown. For example, processor 172 may receive an input signal containing information about treatments provided to the subject from user interface 180. Additional input signals may be used by processor 172 in any of the calculations or operations it performs in accordance with back end processing circuitry 170 or monitor 104.

Memory 174 may include any suitable computer-readable media capable of storing information that can be interpreted by processor 172. In some embodiments, memory 174 may store calculated values, such as pulse rate, blood pressure, blood oxygen saturation, fiducial point locations or characteristics, initialization parameters, venous signals, systemic vascular resistance, mean arterial pressure, cardiac output, central venous pressure, oxygen demand, adaptive filter parameters, any other calculated values, or any combination thereof, in a memory device for later retrieval. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system. Back end processing circuitry 170 may be communicatively coupled with user interface 180 and communication interface 190.

User interface 180 may include user input 182, display 184, and speaker 186. User interface 180 may include, for example, any suitable device such as one or more medical devices (e.g., a medical monitor that displays various physiological parameters, a medical alarm, or any other suitable medical device that either displays physiological parameters or uses the output of back end processing 170 as an input), one or more display devices (e.g., monitor, personal digital assistant (PDA), mobile phone, tablet computer, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

User input 182 may include any type of user input device such as a keyboard, a mouse, a touch screen, buttons, switches, a microphone, a joy stick, a touch pad, or any other suitable input device. The inputs received by user input 182 can include information about the subject, such as age, weight, height, diagnosis, medications, treatments, and so forth.

In an embodiment, the subject may be a medical patient and display 184 may exhibit a list of values which may generally apply to the patient, such as, for example, age ranges or medication families, which the user may select using user input 182. Additionally, display 184 may display, for example, an estimate of a subject's blood oxygen saturation generated by monitor 104 (e.g., an "SpO$_2$" measurement), pulse rate information, respiration rate and/or effort information, blood pressure information, hemoglobin concentration information, a venous signal, systemic vascular resistance, mean arterial pressure, cardiac output, central venous pressure, oxygen demand, any other parameters, and any combination thereof. Display 184 may include any type of display such as a cathode ray tube display, a flat panel display such as a liquid crystal display or plasma display, or any other suitable display device. Speaker 186 within user interface 180 may provide an audible sound that may be used in various embodiments, such as for example, sounding an audible alarm in the event that a patient's physiological parameters are not within a predefined normal range.

Communication interface 190 may enable monitor 104 to exchange information with external devices. Communications interface 190 may include any suitable hardware, software, or both, which may allow monitor 104 to communicate with electronic circuitry, a device, a network, a server or other workstations, a display, or any combination thereof. Communications interface 190 may include one or more receivers, transmitters, transceivers, antennas, plug-in connectors, ports, inputs, communications buses, communications protocols, device identification protocols, any other suitable hardware or software, or any combination thereof. Communications interface 190 may be configured to allow wired communication (e.g., using USB, RS-232, Ethernet, or other standards), wireless communication (e.g., using WiFi, IR, WiMax, BLUETOOTH, USB, or other standards), or both. For example, communications interface 190 may be configured using a universal serial bus (USB) protocol (e.g., USB 2.0, USB 3.0), and may be configured to couple to other devices (e.g., remote memory devices storing templates) using a four-pin USB standard Type-A connector (e.g., plug and/or socket) and cable. In some embodiments, communications interface 190 may include an internal bus such as, for example, one or more slots for insertion of expansion cards.

It will be understood that the components of physiological monitoring system 100 that are shown and described as separate components are shown and described as such for illustrative purposes only. In some embodiments the functionality of some of the components may be combined in a single component. For example, the functionality of front end processing circuitry 150 and back end processing circuitry 170 may be combined in a single processor system. Additionally, in some embodiments the functionality of some of the components of monitor 104 shown and described herein may be divided over multiple components. For example, some or all of the functionality of control circuitry 110 may be performed in front end processing circuitry 150, in back end processing circuitry 170, or both. In addition, while a single processor is depicted in FIG. 1, it will be understood that one or more processors may be used to perform the functionality described above. In other embodiments, the functionality of one or more of the components may be performed in a different order or may not be required. In an embodiment, all of the components of physiological monitoring system 100 can be realized in processor circuitry.

Figure 3:
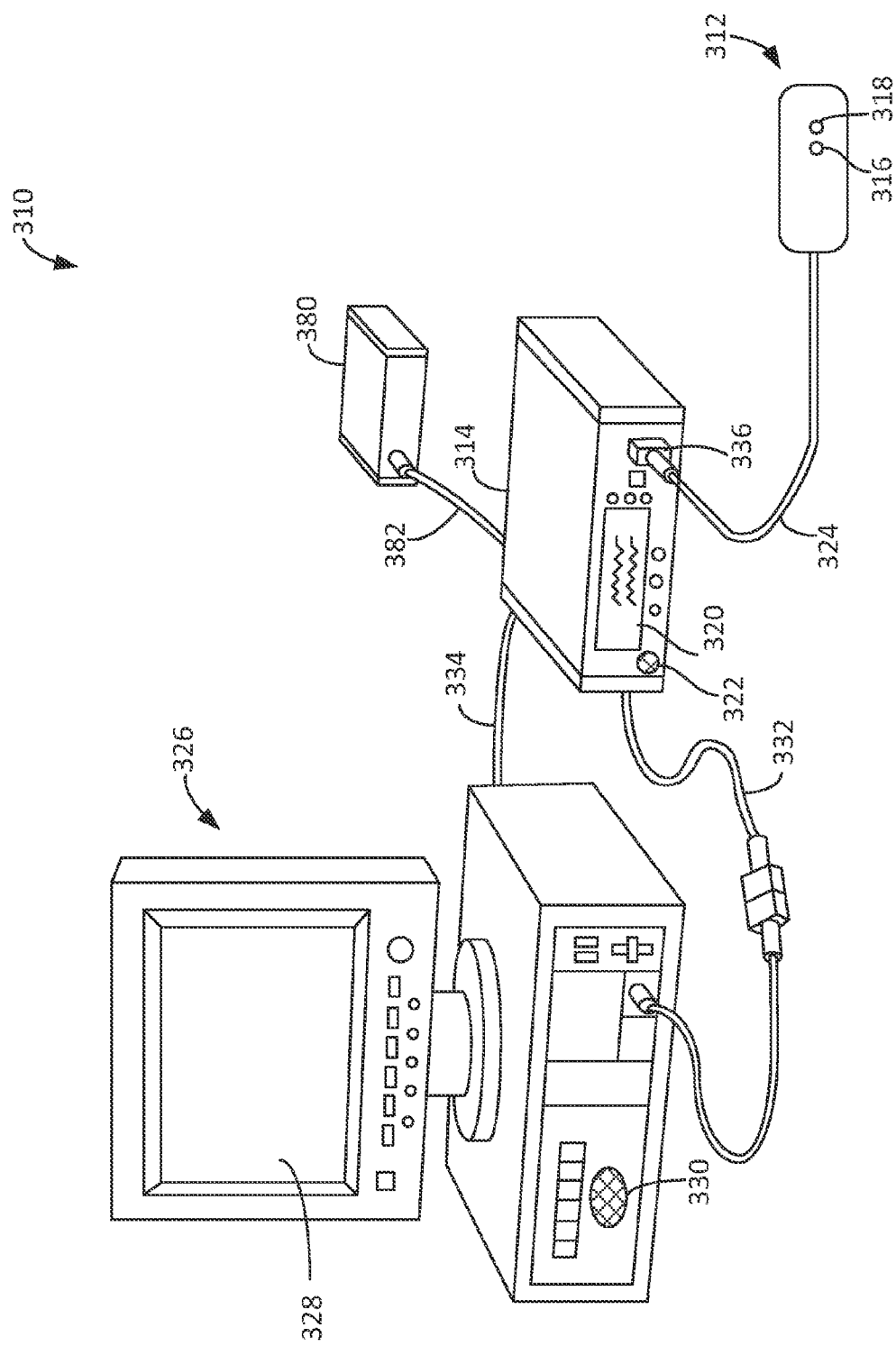
FIG. 3 is a perspective view of an illustrative physiological monitoring system in accordance with some embodiments of the present disclosure.

FIG. 3 is a perspective view of an illustrative physiological monitoring system 310 in accordance with some embodiments of the present disclosure. In some embodiments, one or more components of physiological monitoring system 310 may include one or more components of physiological monitoring system 100 of FIG. 1. Physiological monitoring system 310 may include sensor unit 312 and monitor 314. In some embodiments, sensor unit 312 may be part of an oximeter. Sensor unit 312 may include one or more light source 316 for emitting light at one or more wavelengths into a subject's tissue. One or more detector 318 may also be provided in sensor unit 312 for detecting the light that is reflected by or has traveled through the subject's tissue. Any suitable configuration of light source 316 and detector 318 may be used. In an embodiment, sensor unit 312 may include multiple light sources and detectors, which may be spaced apart. Physiological monitoring system 310 may also include one or more additional sensor units (not shown) that may, for example, take the form of any of the embodiments described herein with reference to sensor unit 312. An additional sensor unit may be the same type of sensor unit as sensor unit 312, or a different sensor unit type than sensor unit 312 (e.g., a photoacoustic sensor). Multiple sensor units may be capable of being positioned at two different locations on a subject's body. In an example, an oximeter sensor may be located at a first position and a thermodilution sensor may be located at a second location. In another example, an oximeter sensor and a temperature sensor may be located near to one another or in the same structure.

In some embodiments, sensor unit 312 may be connected to monitor 314 as shown. Sensor unit 312 may be powered by an internal power source, e.g., a battery (not shown). Sensor unit 312 may draw power from monitor 314. In another embodiment, the sensor may be wirelessly connected (not shown) to monitor 314. Monitor 314 may be configured to calculate physiological parameters based at least in part on data relating to light emission and light detection received from one or more sensor units such as sensor unit 312. For example, monitor 314 may be configured to determine pulse rate, respiration rate, respiration effort, blood pressure, blood oxygen saturation (e.g., arterial, venous, or both), hemoglobin concentration (e.g., oxygenated, deoxygenated, and/or total), a venous signal, systemic vascular resistance, mean arterial pressure, cardiac output, central venous pressure, oxygen demand, any other suitable physiological parameters, or any combination thereof. In some embodiments, calculations may be performed on the sensor units or an intermediate device and the result of the calculations may be passed to monitor 314. Further, monitor 314 may include display 320 configured to display the physiological parameters or other information about the system. In the embodiment shown, monitor 314 may also include a speaker 322 to provide an audible sound that may be used in various other embodiments, such as for example, sounding an audible alarm in the event that a subject's physiological parameters are not within a predefined normal range. In some embodiments, physiological monitoring system 310 may include a stand-alone monitor in communication with the monitor 314 via a cable or a wireless network link. In some embodiments, monitor 314 may be implemented as display 184 of FIG. 1.

In some embodiments, sensor unit 312 may be communicatively coupled to monitor 314 via a cable 324 at port 336. Cable 324 may include electronic conductors (e.g., wires for transmitting electronic signals from detector 318), optical fibers (e.g., multi-mode or single-mode fibers for transmitting emitted light from light source 316), any other suitable components, any suitable insulation or sheathing, or any combination thereof. In some embodiments, a wireless transmission device (not shown) or the like may be used instead of or in addition to cable 324. Monitor 314 may include a sensor interface configured to receive physiological signals from sensor unit 312, provide signals and power to sensor unit 312, or otherwise communicate with sensor unit 312. The sensor interface may include any suitable hardware, software, or both, which may be allow communication between monitor 314 and sensor unit 312.

In some embodiments, physiological monitoring system 310 may include calibration device 380. Calibration device 380, which may be powered by monitor 314, a battery, or by a conventional power source such as a wall outlet, may include any suitable calibration device. Calibration device 380 may be communicatively coupled to monitor 314 via communicative coupling 382, and/or may communicate wirelessly (not shown). In some embodiments, calibration device 380 is completely integrated within monitor 314. In some embodiments, calibration device 380 may include a manual input device (not shown) used by an operator to manually input reference signal measurements obtained from some other source (e.g., an external invasive or non-invasive physiological measurement system).

In the illustrated embodiment, physiological monitoring system 310 includes a multi-parameter physiological monitor 326. The monitor 326 may include a cathode ray tube display, a flat panel display (as shown) such as a liquid crystal display (LCD) or a plasma display, or may include any other type of monitor now known or later developed. Multi-parameter physiological monitor 326 may be configured to calculate physiological parameters and to provide a display 328 for information from monitor 314 and from other medical monitoring devices or systems (not shown). For example, multi-parameter physiological monitor 326 may be configured to display an estimate of a subject's blood oxygen saturation and hemoglobin concentration generated by monitor 314. Multi-parameter physiological monitor 326 may include a speaker 330.

Monitor 314 may be communicatively coupled to multi-parameter physiological monitor 326 via a cable 332 or 334 that is coupled to a sensor input port or a digital communications port, respectively and/or may communicate wirelessly (not shown). In addition, monitor 314 and/or multi-parameter physiological monitor 326 may be coupled to a network to enable the sharing of information with servers or other workstations (not shown). Monitor 314 may be powered by a battery (not shown) or by a conventional power source such as a wall outlet.

In some embodiments, any of the processing components and/or circuits, or portions thereof, of FIGS. 1 and 3, including sensors 102 and 312 and monitors 104, 314, and 326, may be referred to collectively as processing equipment. For example, processing equipment may be configured to amplify, filter, sample and digitize an input signal from sensor 102 or 312 (e.g., using an analog-to-digital converter), and calculate physiological information from the digitized signal. Processing equipment may be configured to generate light drive signals, amplify, filter, sample and digitize detector signals, sample and digitize other analog signals, calculate physiological information from the digitized signal, perform any other suitable processing, or any combination thereof. The processing equipment may include one or more processors. In some embodiments, all or some of the components of the processing equipment may be referred to as a processing module.

Figure 4:
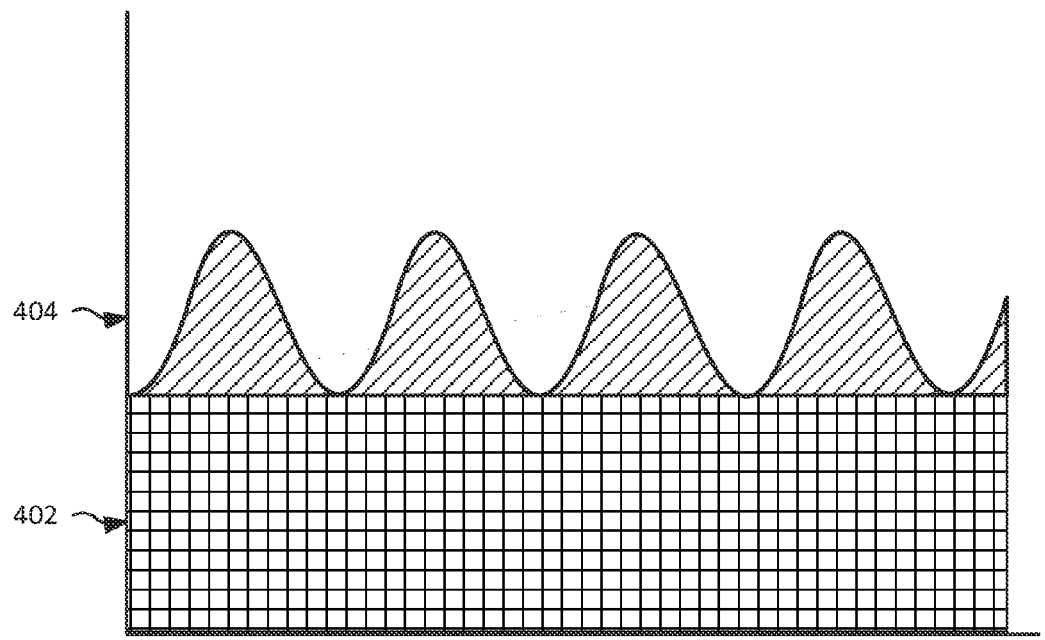
FIG. 4 shows an illustrative plot of AC and DC signals in accordance with some embodiments of the present disclosure.

FIG. 4 shows illustrative plot 400 including AC and DC signals in accordance with some embodiments of the present disclosure. Plot 400 includes waveform 402. In some embodiments, the signal amplitudes that correspond to waveform 402 may be considered to include an AC component and a DC component. It will be understood that waveform 402 does not necessarily correspond to a physiological signal, but rather is shown to illustrate the usage of the DC and AC signal terminology used herein. It will also be understood that AC and DC need not refer to the traditional electrical power definitions. Rather, DC may refer to the portion of the signal that is relatively constant over time, while AC may refer to the portion of the signal that changes in time. For example, the AC component may vary substantially with a cardiac cycle. In the illustrated example, shaded region 404 may correspond to the AC signal component of waveform 402, and shaded region 406 may correspond to a DC signal component of waveform 402. It will be understood that the particular division of AC and DC component parts of a signal shown in plot 400 is merely exemplary and that any suitable definitions may be used. For example, in some embodiments the DC level may be identified at an initial point and remain constant for a predefined interval. In another example, the DC level may track the lowest point of the AC oscillation and be updated at regular intervals such as every pulse, every $10^{th}$ pulse, every 10 seconds, or any other suitable interval. In some embodiments, the interval may vary based on parameters such as patient condition. In some embodiments, the DC component of a received PPG signal may correspond to the amount of light received at diastole, and the AC component may correspond to the variations above the diastole level.

Figure 5:
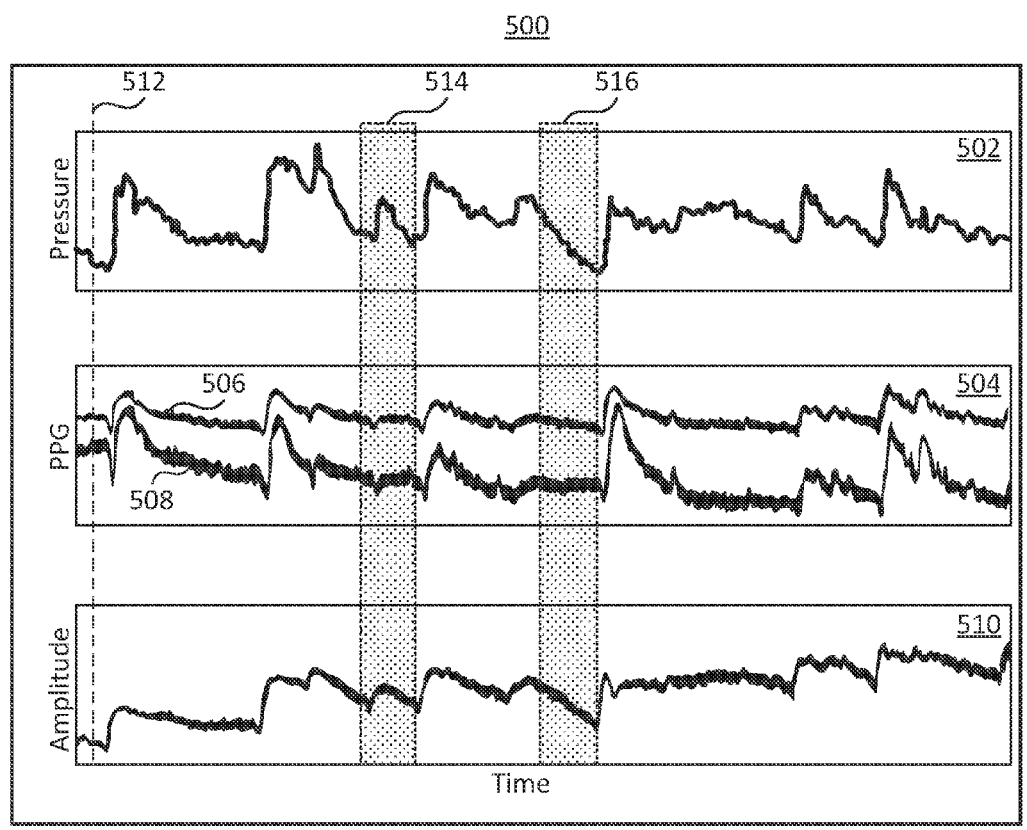
FIG. 5 shows an illustrative plot window of signals in accordance with some embodiments of the present disclosure.

FIG. 5 shows illustrative plot window 500 including signals in accordance with some embodiments of the present disclosure. Plot window 500 includes pressure plot 502, PPG plot 504, and venous signal plot 510. The x-axes of the plots are in units of time and share a common scale. For example, the x-axes may represent 60 minutes of data monitoring. In some embodiments, plot window 500 shows that the data of venous signal plot 510 follows the data of pressure plot 502 more closely than that of PPG plot 504.

Pressure plot 502 includes a section of blood pressure measurement information of a subject. For example, blood pressure may be continuously monitored using a catheter or other invasive devices, a non-invasive technique, any other suitable technique, or any combination thereof. In some embodiments, pressure plot 502 indicates the mean arterial pressure of a subject measured over the course of 1 hour. The y-axis is in units of pressure, for example millimeters of mercury.

PPG plot 504 includes photoplethysmographic signals. Red signal 506 is indicative of detected light signals that correspond to a red wavelength light after interacting with a subject. IR signal 508 corresponds to an IR detected signal. In an example, red signal 506 and IR signal 508 may be detected by detector 140 of FIG. 1.

Venous signal plot 510 includes a signal calculated based on the information contained in PPG plot 504. The signal in plot 510 may be plotted using the expression:

$$\left(\frac{\Delta I_{R,DC}}{I_{R,DC}}\right) - R\left(\frac{\Delta I_{IR,DC}}{I_{IR,DC}}\right) \qquad (22)$$

where the DC components of the PPG signals are used. The change in the DC signal may be, for example, calculated relative to an initial value at time point 512. That is to say, the value of the signal at time point 512 (or any other suitable point) may be used as a baseline value, and the difference between that baseline and the current may be used as $\Delta I$. In another example, the change may be determined based on a moving baseline such as a moving average, based on the change between successive data points, based on a predetermined baseline, based on user input, based on any other suitable technique, or any combination thereof.

In some embodiments, the venous signal of plot 510 may include features corresponding to changes in blood pressure that are not visible in the PPG signals of plot 504. In an example, in region 514 the pressure signal of plot 502 shows a rise and fall. This rise and fall is also reflected in the venous signal of plot 510. The rise and fall does not, however, appear in the PPG signals of plot 504. In another example, in region 516 the pressure is continuously decreasing. The venous signal of plot 510 shows a similar decrease. The PPG signals of plot 504, however, remain relatively constant. Thus in some embodiments, the venous signal may track changes in blood pressure.

In some embodiments, a venous signal such as that shown in plot 510 may correspond to blood pressure changes in a subject. In some embodiments, the information may be used, for example, to continuously determine blood pressure without the use of an invasive catheter or other measurement. In some embodiments, the venous signal may track and/or be proportional to changes in the blood pressure, but may not provide an absolute measurement. The venous signal may be combined with additional signals in order to accurately determine blood pressure values. In an example, information from a venous signal may be used in combination with another blood pressure measurement such as a manual or automatic auscultatory measurement, such as with a blood pressure cuff. For example, an auscultatory measurement may be used to determine a value of blood pressure, and changes from that value may be based on changes in a venous signal. In another example, changes in a venous signal may be used to trigger a measurement event such as a calibration event. Calibration may include taking an auscultatory measurement and using that information to calibrate a continuous monitoring system such as one based on a venous signal, a Doppler signal, any other suitable information, or any combination thereof.

In some embodiments, the venous DC signal such as that used in expression (22) may provide pressure information because where the oxygen saturation and cardiac output remain relatively constant, changes in the venous signal may correspond primarily to changes in blood volume. Assuming constant vasocompliance, changes in volume may correspond to changes in pressure. That is, for tissues with low oxygen uptake, stable $SpO_2$ (where venous concentrations remain relatively constant), and stable vasocompliance, changes in the venous path length $d_{ven}$ may be reflected in changes in the effective venous signal, and thus the changes in the venous signal can be used to track pressure as shown in plot window 500.

It will be understood that a venous signal may be used to determine physiological properties alternatively or in addition to pressure. For example, a venous signal may be used to estimate changes in systemic vascular resistance, mean arterial pressure, cardiac output, central venous pressure, oxygen demand, may be used as an input to an adaptive filter, may be used for any other suitable purpose, or any combination thereof.

In some embodiments, a venous signal may be used to estimate changes in systemic vascular resistance (SVR), sometimes referred to as vasotone. In some embodiments, vasotone is inversely proportional to vasocompliance. In some embodiments, changes in a venous signal may correspond to changes in vasotone. For example, where the pressure and $SpO_2$ are relatively stable, changes in the venous signal may correspond to changes in the SVR. Pressure and $SpO_2$ may remain relatively constant, for example, in peripheral tissues. In some embodiments, peripheral vasotone may be used to monitor SVR by monitoring changes in the venous path length which may decrease with changing vasotone and/or by monitoring hemoglobin concentrations which may increase with increasing vasotone. In some embodiments, the SVR may be used in an estimate of cardiac output (CO), for example using the equation:

$$CO = \frac{SVR}{MAP} \quad (23)$$

where CO is the cardiac output, SVR is the systemic vascular resistance, and MAP is the mean arterial pressure. In an example, SVR may be determined using a venous signal, MAP may be determined using an intravenous arterial catheter, and CO may be thus calculated. In another example, where the central venous pressure (CVP) is also known, cardiac output may be more accurately estimated using the following equation:

$$CO = \frac{SVR - CVP}{MAP} \quad (24)$$

In some embodiments, a venous signal may be used to determine a central venous pressure and/or a systemic venous resistance. This information may be used to determine an estimate of mean arterial pressure or other parameters based on the following equation:

$$MAP = CO \cdot SVR + CVP \quad (25)$$

In some embodiments, different elements of equation (25) may be determined by different techniques depending on the available information, and the venous signal may be used to provide otherwise unknown information. In an example, the venous signal may be used to determine SVR, while cardiac output and CVP are determined based on other sensing techniques, in order to calculate MAP. In another example, MAP may be determined using an intravenous catheter, CO may be determined using a thermodilution technique, and SVR may be determined based on the venous signal. This information may be used to calculate CVP. In another example, the venous signal may be used to determine SVR, and this information may be used to determine a confidence metric corresponding to the estimate of MAP or CO based on equation (25). It will be understood that the aforementioned is merely exemplary and that the venous signal may be used to provide information corresponding to any physiological parameter to which it is related.

In some embodiments, a venous signal may be used in determining oxygen demand. In an example, if the venous signal is found to correspond to a substantially constant volume at the sample site (e.g., cardiac output and vasocompliance are both substantially constant), then changes in the venous signal may correspond to oxygen concentration changes associated with changes in oxygen demand. This may, for example, be used in determining oxygen demand of certain organs, such as the brain.

In some embodiments, a venous signal may be used an input signal for an adaptive filter. For example, a venous signal may be provided as a reference signal to adaptively filter a PPG signal, in order to remove any changing venous signal component. Thus, after adaptively filtering to remove a venous component, the filtered signal may substantially contain arterial information. The filtered signal may be used to determine physiological parameters such as $SpO_2$ more accurately than if it had not been filtered. For example, a change in a venous contribution to a PPG signal may distort a blood oxygen saturation measurement, and filtering that contribution out of the signal may improve the blood oxygen saturation determination. Adaptive filterers may include, for example, a digitally-implemented correlation canceller or adaptive noise canceller that uses the venous signal as an input to determine one or more filtering coefficients. The filtering coefficients may be combined with a physiological signal in order to reduce the unwanted contributions. In some embodiments, filter coefficients may be adaptively updated to minimize the presence of frequency components of the reference signal in the filtered signal.

Figure 6:
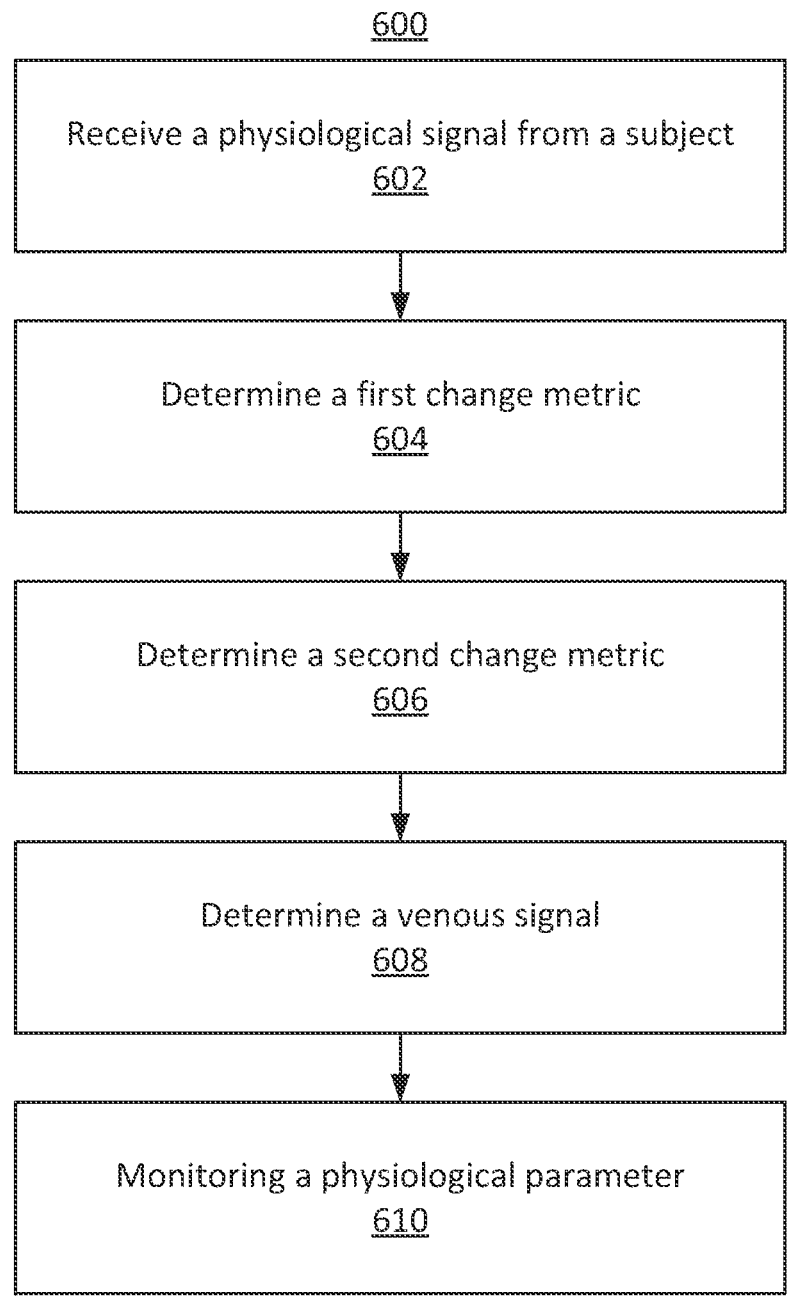
FIG. 6 shows an illustrative flow diagram including steps for generating a venous signal in accordance with some embodiments of the present disclosure.

FIG. 6 shows illustrative flow diagram 600 including steps for generating a venous signal in accordance with some embodiments of the present disclosure.

Step 602 includes receiving a physiological signal from a subject. The physiological signal may include a first component corresponding to a first wavelength of light and a second component corresponding to a second wavelength of light. In some embodiments, the physiological signal may include a PPG signal. In some embodiments, the physiological signal may be detected by detector 140 of FIG. 1. In some embodiments, the physiological signal may include detector current waveform 214 of FIG. 2. It will be understood that the received physiological signals may include signals received at a detector such as detector 140 of FIG. 1, signals received by a monitor such as monitor 104 of FIG. 1, signals received at backend processing such as back end processing circuitry 170 of FIG. 1, any other suitable signals, or any combination thereof.

In an example, a pulse oximeter may provide a light signal to a subject. The light signal may include time-multiplexed red and IR light pulses. The light may interact with a subject and be partially attenuated. The attenuated light signal may be detected using a photodetector, which may generate a current signal that corresponds to the intensity of detected light.

Step 604 includes determining a first change metric. The first change metric may be determined based on changes in a baseline of the first component of the physiological signal. In some embodiments, the first change metric may be based on a ratio of the change in amplitude of the first component corresponding to a first wavelength of light to the amplitude of the first component of light. In some embodiments, the first change metric may include the expression:

$$\left(\frac{\Delta I_{\lambda_1,DC}}{I_{\lambda_1,DC}}\right) \tag{26}$$

where $\lambda_1$ corresponds to a first wavelength of light, $I_{\lambda_1,DC}$ corresponds to the intensity of the DC component of the first wavelength of light, and $\Delta I_{\lambda_1,DC}$ corresponds to the change in the intensity of the DC signal. In some embodiments, the first change metric may correspond to the first term of expression (22), where $\lambda_1$ corresponds to a red light wavelength. It will be understood that any suitable wavelength or combination of wavelengths may be used. The change in light intensity $\Delta I$ may be determined using any suitable technique, such as those described with respect to plot window 500 of FIG. 5. For example, the change may be determined with respect to a baseline that is established at any suitable point, with respect to a moving average, with respect to prior data points, using any other suitable technique, or any combination thereof.

Step 606 includes determining a second change metric. The second change metric may be determined based on changes in a baseline of the second component of the physiological signal. The second change metric may additionally or alternatively be based on a coefficient associated with arterial oxygen saturation. In some embodiments, the second change metric may be based on the expression:

$$R\left(\frac{\Delta I_{\lambda_2,DC}}{I_{\lambda_2,DC}}\right) \tag{27}$$

where R is a coefficient associated with arterial oxygen saturation, $\lambda_2$ corresponds to a second wavelength of light, $I_{\lambda_2,DC}$ corresponds to the intensity of the DC component of the first wavelength of light, and $\Delta I_{\lambda_2,DC}$ corresponds to the change in the intensity of the DC component. In some embodiments, R corresponds to the ratio-of-ratios calculation. In some embodiments, for example when the system is implemented in a pulse oximeter, R may be obtained from an oximetry algorithm. In some embodiments, the second change metric may correspond to the second term of expression (22), where $\lambda_2$ corresponds to an IR light wavelength. It will be understood that any suitable wavelength or combination of wavelengths may be used. The change in light intensity $\Delta I$ may be determined using any suitable technique, for example as described above in step 606.

Step 608 includes determining a venous signal. The venous signal may be based on the first change metric of step 604 and the second change metric of step 606. The venous signal may be indicative of changes associated with venous blood. In some embodiments, the venous signal is determined based on the expression:

$$\left(\left(\frac{\Delta I_{\lambda_1,DC}}{I_{\lambda_1,DC}}\right) - R\left(\frac{\Delta I_{\lambda_2,DC}}{I_{\lambda_2,DC}}\right)\right) \tag{28}$$

where the venous signal is calculated as the difference between the first change metric and the second change metric. In some embodiments, by subtracting the second change metric from the first change metric, arterial contributions may be substantially cancelled out. Thus, subtracting the second change metric from the first change metric may result in a signal that corresponds substantially to venous information.

Step 610 includes monitoring a physiological parameter. In some embodiments, monitoring includes determining the physiological parameter based on the venous signal of step 608. The physiological parameter may include blood pressure, systemic vascular resistance, cardiac output, central venous pressure, mean arterial pressure, any other suitable parameter, or any combination thereof. Physiological parameters may be determined as described above with relation to plot window 500 of FIG. 5.

In some embodiments, monitoring includes triggering an event (e.g., a determination of physiological parameter) based on the venous signal. In some embodiments, triggering the event includes triggering a calibration of a physiological parameter. In some embodiments, the triggering may include triggering a calibration of a blood pressure calculation. For example, the system may monitor blood pressure intermittently using an automatic auscultatory technique, and continuously based on the venous signal. When the venous signal-derived blood pressure measurement deviates by a particular amount from the prior calibration level, the system may trigger an auscultatory technique, and use that blood pressure information to recalibrate the venous-derived measurement.

In some embodiments, a venous signal trigger may be used in combination with an automatic blood pressure monitoring signal. In some automatic blood pressure monitoring systems, auscultatory blood pressure measurements may be made at regular intervals, for example, every 5 minutes. By monitoring changes in the venous signal, the interval at which auscultatory measurements are performed may be modified. For example, when the venous signal shows changing conditions of the subject, auscultatory blood pressure measurements may be performed more frequently, while under stable conditions, measurements may be performed less frequently. In some embodiments, a trigger may occur based on a percent change threshold crossing of the venous signal. In some embodiments, a trigger may occur based on a rate of change of the venous signal. In some embodiments, a trigger may begin an auscultatory blood pressure measurement. In some embodiments, a trigger may cause an update in a measurement interval.

In some embodiments, triggering an event may include generating an alarm based on the venous signal. Alarms may include audio, textual, or processing alarms. Alarms may include a message to a user, may trigger a measurement, may trigger a medical procedure, may include any other suitable action, or any combination thereof.

It will be understood that the aforementioned steps of flow diagram 600 are exemplary and that in some implementations, steps may be added, removed, omitted, repeated, reordered, modified in any other suitable way, or any combination thereof. It will also be understood that the aforementioned mathematical expressions are merely exemplary and that any suitable change metrics, venous signals, coefficients, and other terms may be used. It will also be understood that in some embodiments, the venous signal equations described herein may be modified to compensate for changes in arterial blood. For example, a venous signal used to determine pressure may be compensated for changing oxygen saturation.

The foregoing is merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

What is claimed:

1. A method of processing a physiological signal, the method comprising:
   receiving the physiological signal from a subject, the signal comprising a first component corresponding to a first wavelength of light and a second component corresponding to a second wavelength of light;
   determining, using one or more processors, a first change metric based on a change in a baseline of the first component of the physiological signal;
   determining, using one or more processors, a second change metric based on a change in a baseline of the second component of the physiological signal and based on a coefficient associated with arterial oxygen saturation;
   determining, using one or more processors, a venous signal based on the first change metric and the second change metric, wherein the venous signal is indicative of changes associated with venous blood; and
   monitoring, using one or more processors, a physiological parameter based on the venous signal.

2. The method of claim 1, further comprising:
   determining, using one or more processors, a ratio-of-ratios value based on the received physiological signal, wherein the ratio-of-ratios value is associated with arterial oxygen saturation; and
   determining, using one or more processors, the coefficient based on the ratio-of-ratio value.

3. The method of claim 1, wherein the first change metric is determined based on the following expression:

$$\left(\frac{\Delta I_{\lambda 1, DC}}{I_{\lambda 1, DC}}\right),$$

where $I_{\lambda 1, DC}$ comprises the first component corresponding to the first wavelength of light.

4. The method of claim 1, wherein the second metric signal is determined based on the following expression:

$$R\left(\frac{\Delta I_{\lambda 2, DC}}{I_{\lambda 2, DC}}\right),$$

where $I_{\lambda 2, DC}$ comprises the second component corresponding to the second wavelength of light and R comprises the coefficient associated with arterial oxygen saturation.

5. The method of claim 1, wherein the venous signal is determined based on the following expression:

$$\left(\left(\frac{\Delta I_{\lambda 1, DC}}{I_{\lambda 1, DC}}\right) - R\left(\frac{\Delta I_{\lambda 2, DC}}{I_{\lambda 2, DC}}\right)\right),$$

where:
   $I_{\lambda 1, DC}$ comprises the first component corresponding to the first wavelength of light;
   $I_{\lambda 2, DC}$ comprises the second component corresponding to the second wavelength of light; and
   R comprises the coefficient associated with arterial oxygen saturation.

6. The method of claim 1, wherein the physiological parameter comprises blood pressure.

7. The method of claim 1, wherein the physiological parameter comprises systemic vascular resistance.

8. The method of claim 1, further comprising triggering an event based on the venous signal.

9. The method of claim 8, wherein triggering the event comprises triggering a calibration of a calculation of a physiological parameter.

10. The method of claim 9, wherein the calibration of a calculation of a physiological parameter comprises the calibration of a blood pressure calculation.

11. A system for operating a physiological monitor, the system comprising:
    an input configured for receiving a physiological signal from a subject, the signal comprising a first component corresponding to a first wavelength of light and a second component corresponding to a second wavelength of light; and
    one or more processors configured to perform operations comprising:
        determining a first change metric based on a change in a baseline of the first component of the physiological signal;
        determining a second change metric based on a change in a baseline of the second component of the physiological signal and based on a coefficient associated with arterial oxygen saturation;
        determining a venous signal based on the first change metric and the second change metric, wherein the venous signal is indicative of changes associated with venous blood; and
        determining a physiological parameter based on the venous signal.

12. The system of claim 11, wherein the one or more processors are further configured to perform operations comprising:
 determining a ratio-of-ratios value based on the received physiological signal, wherein the ratio-of-ratios value is associated with arterial oxygen saturation; and
 determining the coefficient based on the ratio-of-ratio value.

13. The system of claim 11, wherein the first change metric is determined based on the following expression:

$$\left(\frac{\Delta I_{\lambda 1,DC}}{I_{\lambda 1,DC}}\right),$$

where $I_{\lambda 1,DC}$ comprises the first component corresponding to the first wavelength of light.

14. The system of claim 11, wherein the second metric signal is determined based on the following expression:

$$R\left(\frac{\Delta I_{\lambda 2,DC}}{I_{\lambda 2,DC}}\right),$$

where $I_{\lambda 2,DC}$ comprises the second component corresponding to the second wavelength of light and R comprises the coefficient associated with arterial oxygen saturation.

15. The system of claim 11, wherein the venous signal is determined based on the following expression:

$$\left(\left(\frac{\Delta I_{\lambda 1,DC}}{I_{\lambda 1,DC}}\right) - R\left(\frac{\Delta I_{\lambda 2,DC}}{I_{\lambda 2,DC}}\right)\right),$$

where:
 $I_{\lambda 1,DC}$ comprises the first component corresponding to the first wavelength of light;
 $I_{\lambda 2,DC}$ comprises the second component corresponding to the second wavelength of light; and
 R comprises the coefficient associated with arterial oxygen saturation.

16. The system of claim 11, wherein the physiological parameter comprises blood pressure.

17. The system of claim 11, wherein the physiological parameter comprises systemic vascular resistance.

18. The system of claim 11, wherein the one or more processors are further configured to perform operations comprising triggering an event based on the venous signal.

19. The system of claim 18, wherein triggering the event comprises triggering a calibration of a calculation of a physiological parameter.

20. The system of claim 19, wherein the calibration of a calculation of a physiological parameter comprises the calibration of a blood pressure calculation.

* * * * *